United States Patent [19]

Napierski

[11] Patent Number: 4,588,874
[45] Date of Patent: May 13, 1986

[54] ELECTRICAL DEVICE FOR EVAPORATING OF ACTIVE SUBSTANCES, PREFERABLY INSECTICIDES

[76] Inventor: Reinhard Napierski, Talstrasse 18, 6361 Niddatal 1, Fed. Rep. of Germany

[21] Appl. No.: 666,176

[22] Filed: Oct. 29, 1984

[30] Foreign Application Priority Data

Nov. 1, 1983 [DE] Fed. Rep. of Germany ....... 3339832

[51] Int. Cl.[4] ........................... A61L 9/03; A01M 1/20
[52] U.S. Cl. .................................... 219/271; 219/273; 219/274; 219/275; 239/136; 239/57
[58] Field of Search .............. 219/271, 272, 273, 274, 219/275, 276; 239/34, 35, 45, 47, 53, 54, 55, 56, 60, 135, 136

[56] References Cited

U.S. PATENT DOCUMENTS

| 2,103,609 | 12/1937 | Bradburn | 239/54 |
| 4,214,146 | 7/1980 | Schimanski | 219/274 |
| 4,391,781 | 7/1983 | van Lit | 219/274 |

FOREIGN PATENT DOCUMENTS 7823826 2/1979 Fed. Rep. of Germany.
8233077 4/1983 Fed. Rep. of Germany.

OTHER PUBLICATIONS

Brown, W. W., "Automatic Disc Loader . . . ", IBM Tech. Disc. Bull., vol. 26, No. 6, Nov. '83, pp. 2724-2725.

Primary Examiner—Clarence L. Albritton
Assistant Examiner—Teresa J. Walberg
Attorney, Agent, or Firm—Larson and Taylor

[57] ABSTRACT

The electrical device for evaporating of active substances, preferably insecticides, contained in carrier tablets, has a housing (10) provided with a magazine (22,24,32) for receiving a variety of carrier tablets (18). A transporting member movably disposed on the housing such as a rotatably cage (32), through movement thereof will transport the stored carrier tablets from the storage position in the magazine into the space between the heating panel (16) and the protective grating (26). In the new device, the carrier tablets need be touched only at major intervals by the operator's fingers.

13 Claims, 11 Drawing Figures

ELECTRICAL DEVICE FOR EVAPORATING OF ACTIVE SUBSTANCES, PREFERABLY INSECTICIDES

The present invention is concerned with an electrical device for evaporating of active substances, preferably insecticides, contained in carrier tablets, comprising a housing provided with a magazine accommodating a variety of carrier tablets, which housing will receive a heating panel covered by a protective grating, with the carrier panels being suitably introduced into the space between heating panel and protective grating.

It is known in the art (DE-GM No. 78 23 826) to store carrier tablets externally of the device in sealed state and to singly introduce them, as required, into the device designed to receive respectively one tablet. For that purpose, it will be necessary for the carrier tablet to be placed into the predetermined position between the heating panel and the protective grating. As a proper positioning of the carrier tablets on the heating panel cannot automatically be attained solely with the aid of the operator's fingers or of lose items such as another carrier tablet, the state-of-the-art device is provided with a frame reciprocable on the housing, having a window opening into which is suitably introduced a single carrier tablet externally of the protective grating. The carrier tablet, if the frame is pushed into its end position defined by a stop underneath the protective grating, will be placed precisely into the proper position on the heating panel. Hence, with the conventional slidable frame it is not only attained—as in the simple introduction of tablets into a slot leading to the heating panel—to safeguard a lateral guidance of the tablets but, in the course of the laterally guided relative movement between carrier tablet and heating panel, also a stoppage of the said movement by stopping at precisely the proper moment so as to push the carrier tablet just sufficiently but not excessively far over the heating panel. In the prior art device, the slidable frame—as compared with the earlier state of art provided with a guiding slot—is a positioning aid preventing the carrier tablet from being pushed away over the heating panel.

According to another conventional suggestion (DE-GM No. 82 33 077), a sealable magazine container is provided in the device as such, which is capable of accommodating a multiplicity of carrier tablets. However, in the prior art design, these carrier tablets will have to be taken manually from the magazine to be introduced by the operator's fingers into the gap between heating panel and protective grating. As the carrier tablets are effective for a relatively short period of time only, replacement thereof will have to be performed substantially every other day, it being inevitable with all prior known devices to physically touch (by one's fingers) the carrier tablets frequently containing toxic substances. Moreover, replacement of the tablets containing the active substances, hitherto, has regularly envolved a complicated procedure to drop the spent tablets into the next waste box.

It is the object of the invention to provide a device of the afore-mentioned type improving the conception of magazining the carrier tablets in the device to the effect that the overall contents of a magazine can successively be used with no need for intermediately touching or removing carrier tablets.

The afore-going problem, in accordance with the invention, is solved by a transportation member movably disposed on the housing through the movement of which the stored carrier tablets are transportable from the storage position in the magazine into the space between heating panel and protective grating.

In accordance with the invention, special importance has been attached to an easy handling of the carrier tablets, in a manner contact-free over an extended period of time. That object is more important that the absolutely precise positioning of the carrier tablets on the heating panel. In the simple practice of the invention, it will, therefore, be sufficient for the transportation member to be so movably disposed on the housing that the entrained carrier tablets are moved past the heating panel. As the carrier tablets and the heating panel can be observed through the protective grating, the setting can be done by visual estimate. That degree of accuracy will be sufficient for the practical application of the invention. This will, of course, not exclude the possibility of providing, if so desired, additional markings forming visual aids, or retaining means forming sensible yet non-compulsory aids, or stops for positioning purposes.

As shown by the following description of a variety of examples of embodiment of devices according to the invention, the transportation member can be, for example, in the form of a drum or disc rotatable relative to the housing, or in the form of a slide. Depending on the selection of the magazine charge, further possibilities of movement of the transporting member can be provided for charging purposes alone in order to expose the storage space or spaces in the magazine. Alternatively, it will, of course, also be possible to fill the magazine through one or more sealable ports on the housing and remove the spent carrier tablets with no need for the transportation member to perform another movement in addition to its actual transportation movement.

Figure 3:
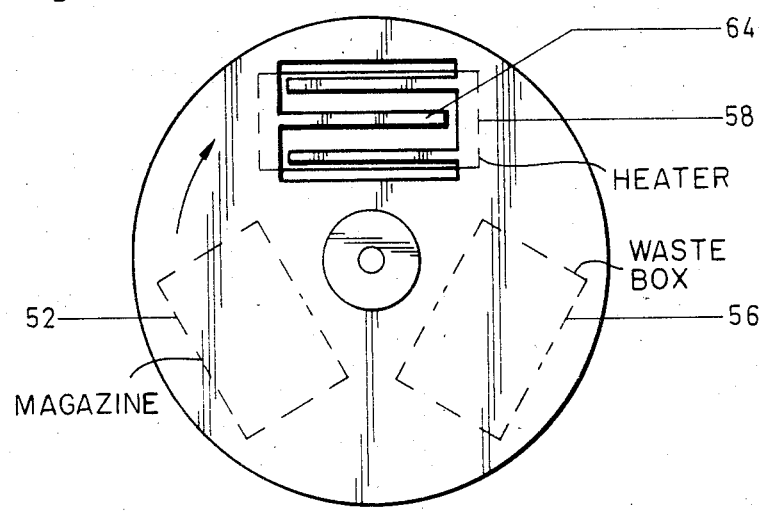
FIGS. 3 and 4 show plan and side views of a device having magazine and waste boxes and a disc-shaped rotatable transportation member for singly transporting the carrier tablets from the magazine box via the space between heater and protective grating to the waste box.
Figure 4:
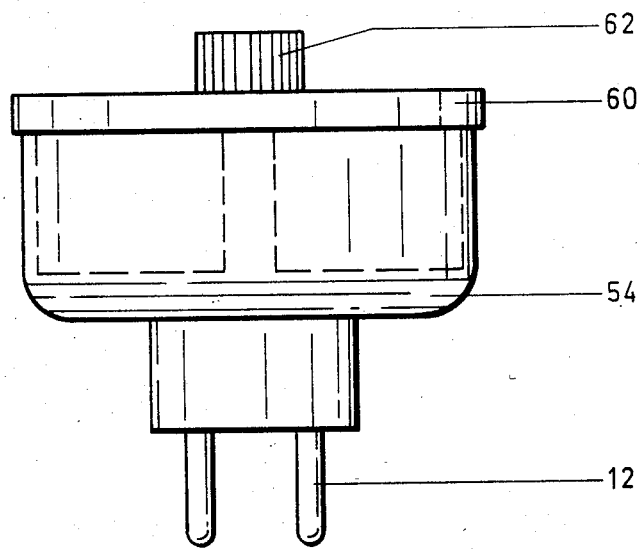
Figure 5A:
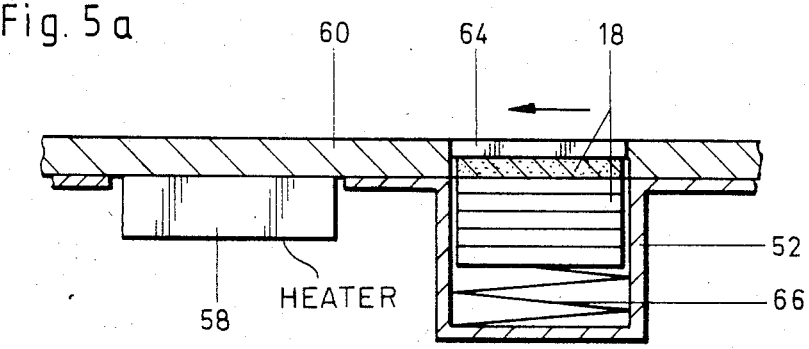
Figure 8:
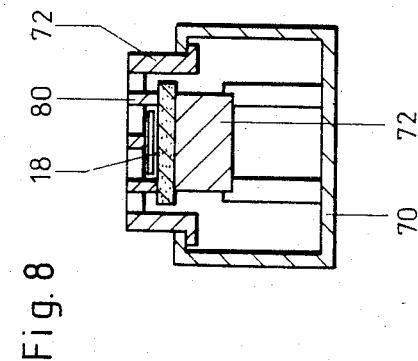
Figure 9:
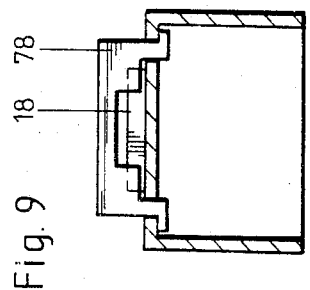
Figure 6:
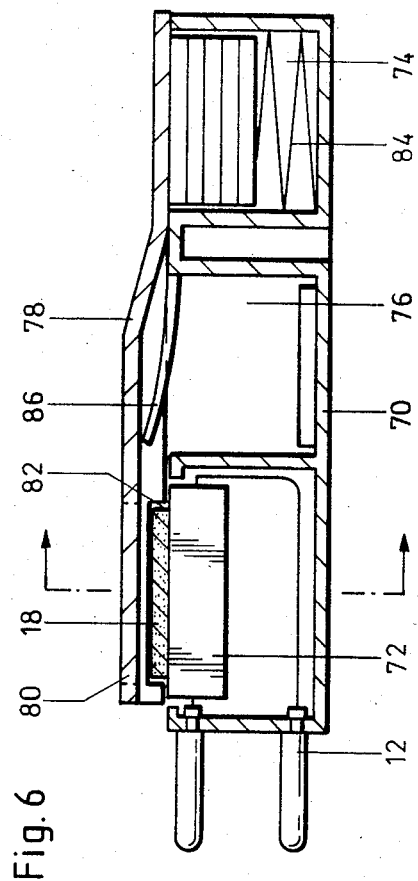
Figure 7:
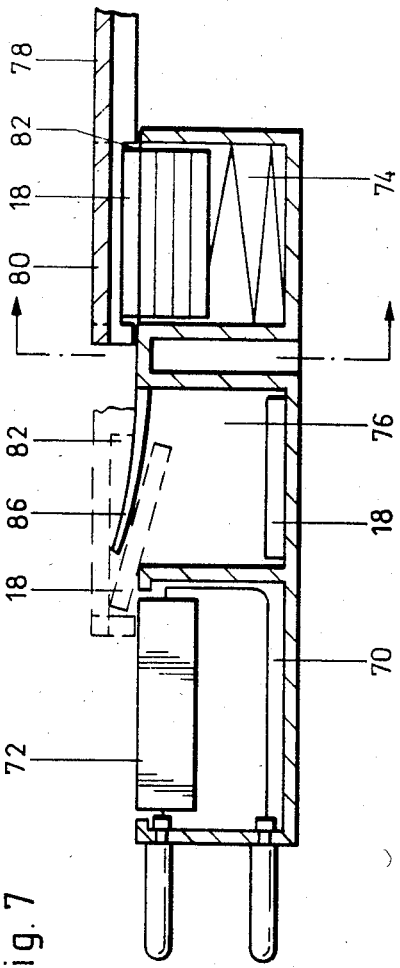

FIGS. 5A, B, C show partial cross-sections through the device according to FIGS. 3 and 4 to illustrate the path of movement of a carrier tablet from magazine to the waste box;

FIGS. 6 and 7 show longitudinal sections through a device having a reciprocable transportation member, in two different positions;

FIGS. 8 and 9 show cross-sections through the device according to FIGS. 6 and 7 following the lines of intersection indicated therein.

Figure 1:
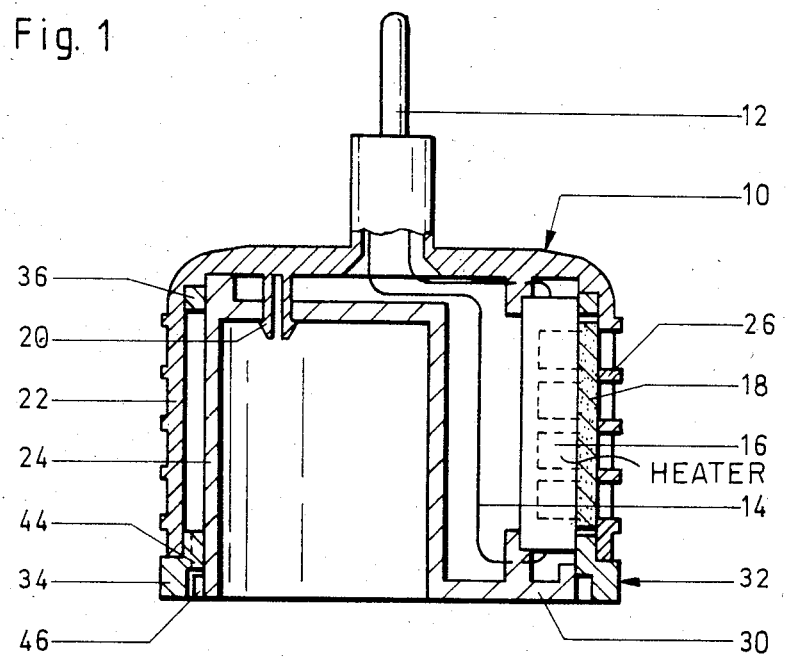
FIGS. 1 and 2 show longitudinal and cross-sections through a device having a drum-type magazine.
Figure 2:
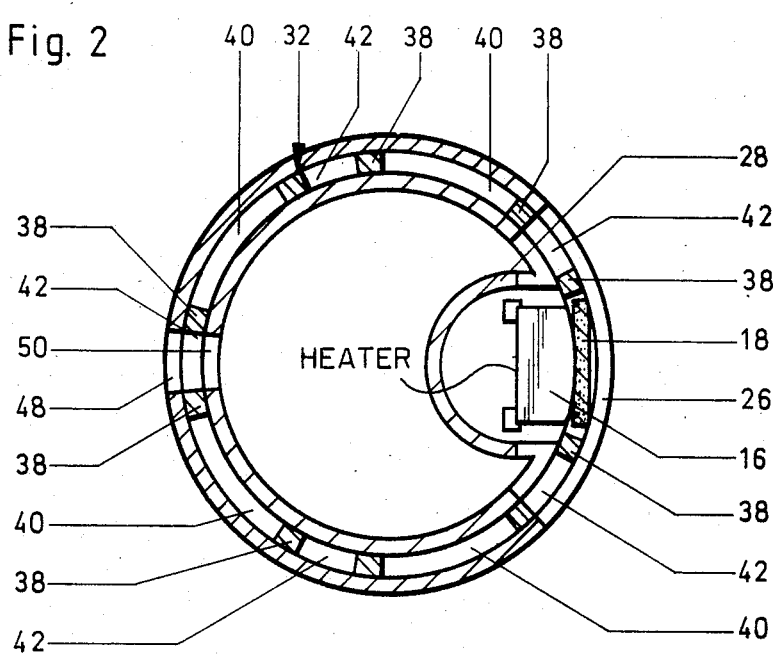

Now, referring to the drawing, FIGS. 1 and 2 thereof show the device comprising a housing 10 having electrical prongs 12 to be plugged into a normal wall socket. Prongs 12 are connected in usual manner, via an electrical line 14, to a heating panel 16 known per se for purposes of this type. A switch may be additionally provided to turn the heating panel on and off or switch over to various heating levels, with the latter being of interest if carrier tablets 18 containing different active substances are to be employed.

In the example of embodiment, housing 10 comprises two housing portions 22, 24 interconnected by a snap or click connector 20, with the housing portions forming an outer and an inner central shell-type wall. While, in the example, the inner housing portion 24 carries the heating panel 16, the outer housing portion 22, at a point of its circumferential wall, is formed as an air-permeable protective grating 26, i.e. in the form of an open window provided with a grating. The heating panel 16 is in radial alignment with the protective grating 26. Incidentally, the heating panel 16, by way of an arching 28 of the inner housing portion 24, is radially inwardly covered. A front-sided closure 30 of the said arching also prevents a contact with the heating panel from the front.

Rotatably guided within the annular space between the shell-type walls of the housing portions 22 and 24 is a cage 32 comprising a front handle ring 34, a rear ring 36 and bridges 38 axially extending between the two rings. The bridges 38, in the example, form five pockets 40 for respectively receiving a carrier tablet 18. The cage 32, respectively between two pockets 40, is provided with a break-out 42 of pocket-type configuration although narrower than a pocket. These break-outs 42 serve as convection openings for ventilating the device when out of operation, with specifically the two break-outs next to the pocket 40 provided between the heating panel 16 and the protective grating 26 preventing the neighboring carrier tablets not yet or no longer in abutment with the heating panel 16, from being heated.

In order to load the drum-type magazine, cage 32 can partly be axially pulled out of the housing 10 forwardly. For this purpose, the front ring 34 is provided with one or several inner grooves shown at 44 in FIG. 1 in broken lines; these grooves can be placed into axial alignment with a corresponding number of stops 46 on housing portion 24, fitting through longitudinal grooves 44. Preferably, grooves 44 and stops 46 will be in alignment only if none of the pockets 40 is positioned between heating panel 16 and protective grating 26. This will prevent children from easily pulling out cage 32 in the axial direction during operation of the device. Suitable outer markings on the housing and on the ring 34 can be indicative of the aligning position between grooves 44 and stop 46.

In the example of embodiment as shown, the shell-type walls of housing 10, equally, have aligning break-outs 48,50 which on either side of the heating panel and diametrically opposite thereto are in alignment with the break-outs 42 in the cage if one of the pockets 40 is positioned between heating panel 16 and protective grating 26.

As revealed by the drawing, among the five pockets 40, in the normal position according to FIG. 2, respectively four pockets are tightly sealed by the inner and outer shell-type walls of the housing, bridges 38 and front ring 34 of the cage, whereas the pocket 40 provided between the heating panel 16 and the protective grating 26 is open to the atmosphere such that the active substances of a carrier tablet 18 evaporated by means of the heating panel, will be passed into the space while the active substances in the carrier tablets accommodated in the sealed pockets 40 will be held therein until also these carrier tablets, by means of handle ring 34 on cage 32, are placed into the position ahead of the heating panel 16.

In order to prevent the carrier tablets 18, upon rotation of the loaded drum magazine, from knocking the edge of the heating panel 16, the latter is rounded off or bevelled at the corner forming the front or rear corner in the direction of rotation. Moreover, a resilient and flexible bearing of the heating panel 16 can be provided to safeguard reliable abutment of the carrier tablets with the heating panel.

To load the magazine of the device according to FIGS. 1 and 2, cage 32 will be drawn out of the casing to the front to such an extent only as to permit five carrier tablets to be manually introduced into the pockets 40 not entirely exposed. In the course thereof, the carrier tablets will already in part be pushed into the annular space between the two housing portions 22 and 24; they will not fall down when the device is rotated in the operator's hand to load all pockets 40. Subsequently, cage 32 will be axially restored into its inner position in the housing, with none of the carrier tablets seated in the pockets 40 properly abutting the heating panel 16 in this position determined by the grooves 44 and the stops 46. However, no difficulties are envolved with rotating a carrier tablet 18 precisely over the heating panel 16 by visual estimate, by turning cage 32 serving as a transportation means, while viewing through protective grating 26.

It will be sufficient, if after the normal period of use, a carrier tablet 18 has been used up, i.e. has become ineffective, to simply turn, by rotating ring 34 relative to housing 10, a fresh carrier tablet contained in another pocket 40 from the magazine ahead of the heater into the operating position. The spent carrier tablets will remain in the device until all carrier tablets have been used up. In the example, no carrier tablet, during a whole week, need be touched by the operator's fingers. Moreover, turning of the cage into the next operative position will be much quicker than replacing of the individual tablets.

The device as shown permits a variety of modifications and extensions. A suitably established connection between prongs 12 and heating panel 16 would permit a stationary configuration of cage 32 and a rotable arrangement of the housing along with the heating panel 16 and the protective grating 26. Also, theoretically, it will be possible to provide a radially outwardly and front-sidedly covered heating panel 16 on the outer housing portion and to arrange the protective grating 26 in the shell-type wall of the inner housing portion 24. Furthermore, it will not be imperative for the carrier tablets 18 to be disposed substantially in the arcuate plane of the shell-type wall of a drum magazine. The said magazine could rather also have the form of a rotatable disc provided with pockets for receiving the carrier tablets, with the housing, in the latter case, being so designed as to arrange the heating panel 16 and the protective grating 26 in axial alignment with both sides of the rotatable disc. The rest of the afore-described properties of the device according to FIGS. 1 and 2 will also apply to a so modified device having a disc-shaped rather than a drum-shaped magazine. In either case, additional means, e.g. flexible members, can be provided on the pockets in order to safely clamp the carrier tablets. Even then, with a suitable design of the shape of the pockets 40 and the clamping between the rings 34,36 and/or bridges 38, removal of the spent carrier tablets will be as simple as in the example as described, i.e. cage 32, in the extreme position thereof, will be drawn from the housing above a waste box while slightly shaking the device. Assistance can also, at any time, be given by the operator's fingers in the event that one of the tablets should stick.

Moreover, extension capabilities are provided by accommodating in the available empty interior of the device according to FIGS. 1 and 2 a motor-powered driving means, e.g. an electro- or clock-spring motor along with a timer indexing the magazine at predetermined timed intervals into the respectively next position until all carrier tablets have been used up.

Figure 5B:
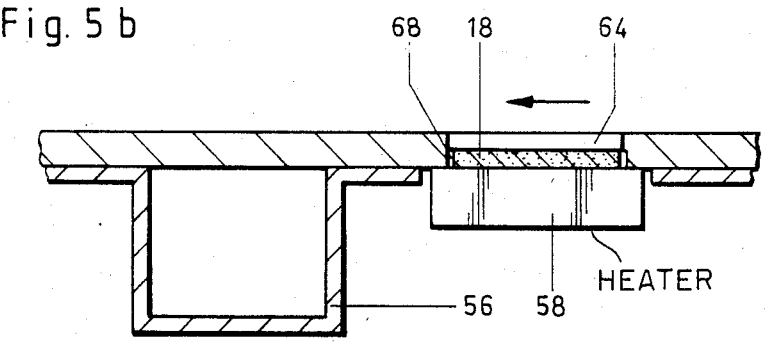

The device according to FIGS. 3 through 5, admittedly, is equally provided with a rotatable transportation member, but it has a common magazine box 52 for all carrier tablets 18 to be stored. In addition thereto, a waste box 56 for spent carrier tablets corresponding to the magazine box 52 is formed in the housing designated by reference numeral 54. Finally, housing 54, in the circular arrangement as shown in FIG. 3, includes a heating panel 58 which, in conventional manner, is connected to the prongs 12 provided in the housing. The transportation member is formed as a disc 60 which is rotatably disposed on the upper side of the housing 54 and which can be rotated, for example, by means of a nonrotationally attached button 62. At one point, disc 60 is perforated and provided with a protective grating 64. As shown by FIG. 5, the protective grating 64 is narrower than the thickness of disc 60 such that respectively one carrier tablet 18, from magazine box 52, under the action of a spring 66 to the protective grate 64, can enter the perforation, hence, forming a pocket designated by 68 in FIG. 5, which is outwardly defined by the protective grating 64.

Figure 5C:
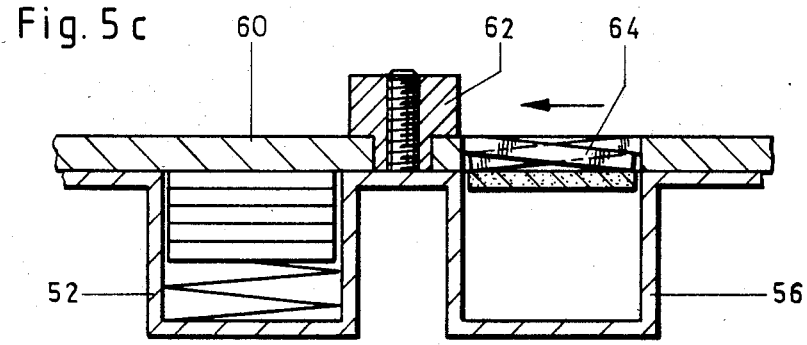

If disc 60 is so set that pocket 68 is precisely above the magazine box 52, spring 66 will force a carrier tablet 18 into pocket 68 as shown in FIG. 5A. Subsequently, disc 60, in the arrow direction of FIG. 3, can be turned to an extent such that pocket 68, with the protective grating 64, is located above the heating panel 58. In that position, the active substance can be evaporated from the carrier tablet by means of the heating panel 58. Disc 60, if the carrier tablet is used up, will be indexed to the next position in the arrow direction according to FIGS. 3 and 5B until pocket 68 has transported the spent carrier tablet 18 from heater 58 to the waste box 56. The spent carrier tablet, as a result of gravity, will fall into the waste box 56. To safeguard the drop thereof, preferably, the protective grating 64 according to FIG. 5C, is formed as resilient bars the spring force of which is weaker than the force of spring 66 but sufficient to force, according to FIG. 5C, the spent carrier tablet 18 from pocket 68 into waste box 56. Pending the drop of the carrier tablet into the waste box 56, the resilient protective grating 64 will force the carrier tablet contained in pocket 68 against the upper sliding surface of the housing and against the heating panel 58, respectively. After all of the carrier tablets having been used up, the rotatable disc 60 can be removed from the housing, the waste box 56 evacuated, and a fresh supply of carrier tablets introduced into the magazine box 52.

It is understood that the supplementary measures referred to in connection with FIGS. 1 and 2, such as means for attaining a cooling convection or a timer, can also be provided in the design according to FIGS. 3 through 5.

The example of embodiment according to FIGS. 6 through 9, shows a device comprising a housing 70 with prongs 12, a heater 72, a magazine box 74 and a waste box 76. The transporting element is a reciprocating slide 78 guided on the housing that, in a manner similar as disc 60, is provided with a break-out in the protective grating 80 (shown in broken lines in FIGS. 6 and 7). Disposed underneath the protective grating 80 is, again, a pocket 82 corresponding to disc 60 into which can be forced by means of a spring 84 a carrier tablet 18, if pocket 82 is located above the magazine box 74.

In the example of embodiment, the waste box 76 is disposed on the path of displacement between magazine box 74 and heater 72. In order to prevent a carrier tablet 18 entrained in pocket 82 from falling on the waste box 76 on its way from the magazine box 74 to the heater 72, the waste box 76 is covered by a resilient flap-type switch 86 which, toward the position as shown in FIG. 6, is resiliently biased; however, if a carrier tablet 18 is passed from the magazine box 74 to the heater 72, it is capable to resiliently escape. Switch 86, if slide 78 is then restored from the position shown in FIG. 6 into that shown in FIG. 7, will seize the spent carrier tablet 18 in the manner as shown in FIG. 7 to lead it to the waste box 76 (see the illustration in broken lines in FIG. 7). The emptied pocket 82 will then be capable, in the position as illustrated in solid lines in FIG. 7, to receive, via magazine box 74, the next fresh carrier tablet 18.

The hook-shaped end of slide 78 laterally defining pocket 82, according to FIG. 7, will be guided past the switch 18 because both parts are not continuously formed along the entire width of a carrier tablet but are rather disposed in staggered relationship with respect to one another. With such a design, it will be possible, as opposed to FIG. 7, to cover heater 72 by a protective grating firmly attached to housing 70 and meshing with the staggered front edge of the slide 78 if the latter is displaced into the position as shown in FIG. 6.

FIGS. 8 and 9 illustrate the arrangement of the aforedescribed parts in cross-section in order to show the manner in which the parts, in a longitudinal movement of the slide 78, are capable of moving one past the other.

What is claimed is:

1. An electrical device for evaporating active substances, such as insecticides, contained in carrier tablets, said device comprising:
    a housing having a drum;
    a heater received by said housing disposed peripherally of said drum;
    a protective grating spaced from and covering at least a part of said heater;
    a drum magazine located on said housing for storing a plurality of the carrier tablets in a storage position located peripherally of said drum, said drum magazine being relatively rotatable with respect to said heater such that a stored carrier tablet can be transported by said relative rotation from the storage position and can be suitably introduced into the space between said heater and said protective grating.

2. A device according to claim 1, characterized in that said drum magazine is formed as a cage rotatably guided in a ring-shaped interspace of a double-walled housing and is provided with a plurality of pockets for receiving the carrier tablets; and that protective grate is disposed on one wall and the heater is disposed on the other wall of said housing.

3. A device according to claim 2, characterized in that said cage is provided with break-outs between said pockets which, in such rotary-angular positions of said cage in which a pocket is provided between said heater and protective grating, are in alignment with a pair of breakouts in the housing walls.

4. A device according to claim 2, characterized in that, in such rotary-angular positions in which a pocket is provided between said heater and said protective grating, said cage and housing walls circumferentially, tightly seal the remaining pockets.

5. A device according to claim 2, characterized in that said cage is axially extractable from said housing at least to such an extent as to permit introduction of carrier tablets into the pockets.

6. A device according to claim 5, characterized in that said cage is extractable from housing only in such rotary-angular positions in which none of the pockets is located between said heater and said protective grating.

7. An electrical device for evaporating active substances, such as insecticides, contained in carrier tablets, said device comprising:
 a housing provided with a magazine that is a pot-shaped container in which carrier tablets when stored therein in a storage position are flatly in abutment with one another;
 a heating panel received by said housing;
 a protective grating spaced from said heating panel such that carrier tablets can be introduced therebetween;
 a transporting member movably located on said housing and provided with an inner pocket for receiving a carrier tablet, said pocket displaceable between said magazine and said heating panel so as to place permanently a received carrier tablet, through the movement of said transporting member from said storage position into said space between said heating panel and protective grating, in communication with the outer atmosphere via the protective grating;
 a pot-shaped waste box into which a tablet entrained in said pocket can be deposited, said pocket being further movable from said magazine past said heating panel to said waste box; and
 spring pressure means for urging carrier tables when stored in said container toward said transporting member.

8. A device as claimed in claim 7 wherein said tablet is deposited in said waste box by gravity.

9. A device as claimed in claim 7 wherein said tablet is deposited in said waste box by spring force.

10. A device as claimed in claim 9 wherein said table is also deposited in said waste box by gravity.

11. A device as claimed in claim 7, characterized in that said transporting member is a disc rotatably disposed on said housing.

12. A device as claimed in claim 7 characterized in that said transporting member is a slide displaceably guided for reciprocating motion on said housing.

13. An electrical device for evaporating active substances, such as insecticides, contained in carrier tablets, said device comprising:
 a housing provided with a magazine that is a pot-shaped container in which carrier tablets when stored therein in a storage position are flatly in abutment with one another;
 a heating panel received by said housing;
 a protective grating spaced from said heating panel such that carrier tablets can be introduced therebetween;
 a transporting member movably located on said housing and provided with an inner pocket for receiving a carrier tablet, said pocket displaceable between said magazine and said heating panel so as to place permanently a received carrier tablet, through the movement of said pocket into said space between said heating panel and protective grating, in communication with the outer atmosphere via the protective grating;
 a pot-shaped waste box into which a carrier tablet entrained in said pocket can be deposited, said pocket being movable from said magazine via a switch past said waste box to said heating panel, and upon backward movement, the entrained carrier tablet can be guided into said waste box through said switch; and
 spring pressure means for urging carrier tablets when stored in said container toward said transporting member.

* * * * *